United States Patent
Phillips et al.

(10) Patent No.: US 9,398,858 B2
(45) Date of Patent: Jul. 26, 2016

(54) SYSTEM FOR BIOMETRIC IDENTITY CONFIRMATION

(71) Applicant: Integrated Monitoring Systems, LLC, Lakewood, CO (US)

(72) Inventors: Brian Kirby Phillips, Lakewood, CO (US); Geoffrey A. Wilson, Roseburg, OR (US)

(73) Assignee: Integrated Monitoring Systems, LLC, Lakewood, CO (US)

( * ) Notice: Subject to any disclaimer, the term of this patent is extended or adjusted under 35 U.S.C. 154(b) by 353 days.

(21) Appl. No.: 13/706,610

(22) Filed: Dec. 6, 2012

(65) Prior Publication Data

US 2013/0150727 A1   Jun. 13, 2013

Related U.S. Application Data

(60) Provisional application No. 61/570,109, filed on Dec. 13, 2011.

(51) Int. Cl.
*G05B 19/00* (2006.01)
*A61B 5/0205* (2006.01)
(Continued)

(52) U.S. Cl.
CPC ............ *A61B 5/0205* (2013.01); *A61B 5/02433* (2013.01); *A61B 5/087* (2013.01);
(Continued)

(58) Field of Classification Search
CPC .. A61B 5/0205; A61B 5/02433; A61B 5/087; A61B 5/117; A61B 5/0059; A61B 5/0876; A61B 5/4845; A61B 5/02055; A61B 5/02405; A61B 5/0452; A61B 5/1455; A61B 5/7267; A61B 7/00; A61B 5/0871; A61B 5/411; A61B 5/7239; A61B 5/021; A61B 5/026; A61B 5/14552; A61B 5/6838; A61B 5/14532; A61B 5/14546; A61B 5/6816; A61B 5/4875; A61B 5/70; A61B 5/7275; A61B 5/024; A61B 5/0075; A61B 5/0088; A61B 5/7225; A61B 5/097; G06F 21/32; G06K 9/00906; G06Q 10/00; G06Q 10/10; G06Q 50/184; G06Q 20/341; G06Q 20/4015; B60K 28/063; H04L 47/10; H04L 47/11; H04L 47/12; H04L 47/263; H04L 47/28; H04L 47/283; H04L 45/00; H04L 45/22; H04L 45/30; H04L 45/306; H04W 36/26; H04W 36/365; G01N 2033/4975; G01N 33/0047; G01N 33/497; B60R 25/04; B60R 25/25; G07C 2009/00095; A47D 13/02; A47D 13/063; A47D 7/002
USPC ........ 600/473, 484, 310, 316, 322; 340/5.82, 340/5.84, 5.52, 573.1, 573.5, 552, 567; 382/124, 115; 235/380, 492, 379, 381
See application file for complete search history.

(56) References Cited

U.S. PATENT DOCUMENTS 3,238,783 A   3/1966 Wright
3,799,149 A   3/1974 Rummel et al.
(Continued)

FOREIGN PATENT DOCUMENTS

EP    0153741 A2    9/1985
WO    94/07407      4/1994

OTHER PUBLICATIONS

PCT International Search Report and Written Opinion for International Application No. PCT/US2012/032014, dated Jul. 27, 2012, 10 pages.

*Primary Examiner* — Mirza Alam
(74) *Attorney, Agent, or Firm* — Dorr, Carson & Birney PC

(57) ABSTRACT

A portable testing unit for biometric identity confirmation includes a housing with an orifice to receive a breath sample from the test subject, a spirometric sensor, and a pulse sensor adjacent to the orifice. A processor analyzes spirometric data from the spirometric sensor and simultaneous pulse wave data from the pulse sensor during the breath sample, together with stored subject characterization data for a known subject to confirm whether the identity of the test subject matches the known subject. A communications link enables the processor to communicate to the external station whether the identity of the test subject matches the known subject. For example, this portable testing unit can be used to control access to a secure facility or computer, authenticate the identity of a party in a financial transaction, or confirm the identity of the subject of an alcohol monitoring test.

9 Claims, 3 Drawing Sheets

(51) Int. Cl.
  *A61B 5/117* (2016.01)
  *A61B 5/024* (2006.01)
  *A61B 5/087* (2006.01)
  *G06F 21/32* (2013.01)
  *G06K 9/00* (2006.01)
  *A61B 5/00* (2006.01)

(52) U.S. Cl.
  CPC ............... *A61B 5/117* (2013.01); *A61B 5/682* (2013.01); *G06F 21/32* (2013.01); *G06K 9/00906* (2013.01); *A61B 5/7225* (2013.01)

(56) References Cited

U.S. PATENT DOCUMENTS

| | | | |
|---|---|---|---|
| 4,346,584 A | 8/1982 | Boehringer | |
| 4,487,055 A | 12/1984 | Wolf | |
| 4,678,057 A | 7/1987 | Elfman et al. | |
| 4,736,619 A | 4/1988 | Legrand | |
| 4,809,810 A | 3/1989 | Elfman et al. | |
| 5,220,919 A | 6/1993 | Phillips et al. | |
| 5,719,950 A | 2/1998 | Osten et al. | |
| 5,739,412 A | 4/1998 | Stock et al. | |
| 5,904,669 A | 5/1999 | Schildgen et al. | |
| 6,379,311 B1 | 4/2002 | Gaumond et al. | |
| 6,483,929 B1 | 11/2002 | Murakami et al. | |
| 6,923,040 B2 | 8/2005 | Stock | |
| 6,967,581 B2* | 11/2005 | Karsten | 340/576 |
| 6,985,070 B1 | 1/2006 | Parker | |
| 6,993,378 B2 | 1/2006 | Wiederhold et al. | |
| 7,002,477 B1 | 2/2006 | Camhi | |
| 7,329,390 B2 | 2/2008 | Stock et al. | |
| 7,388,493 B2 | 6/2008 | Lerch et al. | |
| 7,441,123 B2 | 10/2008 | Grant et al. | |
| 7,536,557 B2 | 5/2009 | Murakami et al. | |
| 7,541,192 B2 | 6/2009 | Stock | |
| 7,554,666 B2 | 6/2009 | Russell | |
| 7,603,887 B2 | 10/2009 | Schlichte | |
| 7,609,145 B2 | 10/2009 | Martis et al. | |
| 7,611,461 B2 | 11/2009 | Hawthorne et al. | |
| 7,616,123 B2 | 11/2009 | Ridder et al. | |
| 7,641,611 B2 | 1/2010 | Hawthorne et al. | |
| 7,756,558 B2 | 7/2010 | Ridder et al. | |
| 7,796,013 B2 | 9/2010 | Murakami et al. | |
| 7,823,681 B2 | 11/2010 | Crespo et al. | |
| 2003/0135097 A1* | 7/2003 | Wiederhold et al. | 600/301 |
| 2004/0236199 A1 | 11/2004 | Hawthorne et al. | |
| 2004/0239510 A1 | 12/2004 | Karsten | |
| 2005/0081639 A1 | 4/2005 | Gourlay | |
| 2007/0063816 A1* | 3/2007 | Murakami | G07F 7/1008 340/5.82 |
| 2007/0177770 A1 | 8/2007 | Derchak et al. | |
| 2009/0240161 A1* | 9/2009 | Sutton | A61B 5/087 600/538 |
| 2009/0253130 A1 | 10/2009 | Yoo | |
| 2009/0275852 A1 | 11/2009 | Oki et al. | |
| 2009/0278659 A1 | 11/2009 | Barzaga Castellanos et al. | |
| 2010/0030041 A1* | 2/2010 | Bruinsma et al. | 600/322 |
| 2010/0108425 A1* | 5/2010 | Crespo | A61B 5/082 180/272 |
| 2010/0277696 A1* | 11/2010 | Huebner | B60K 35/00 352/81 |
| 2011/0009762 A1 | 1/2011 | Eichler et al. | |
| 2011/0090048 A1 | 4/2011 | Li et al. | |
| 2012/0272713 A1* | 11/2012 | Kountotsis | G01N 33/497 73/23.3 |

* cited by examiner

SYSTEM FOR BIOMETRIC IDENTITY CONFIRMATION

RELATED APPLICATION

The present application is based on and claims priority to the Applicant's U.S. Provisional Patent Application 61/570,109, entitled "System For Biometric Identity Confirmation," filed on Dec. 13, 2011.

BACKGROUND OF THE INVENTION

1. Field of the Invention

The present invention relates generally to the field of biometric identity confirmation. More specifically, the present invention discloses a system for biometric identity confirmation based on both spirometric data and pulse wave data.

2. Background of the Invention

Biometric identification is the process of recognizing or rejecting an unknown person as a particular member of a previously characterized set, based on biological measurements. The ideal biometric characterization is specific to the individual, difficult to counterfeit, robust to metabolic fluctuations, insensitive to external conditions, easily measured, and quickly processed.

Fingerprint, retinal, iris, and facial scans are well-known biometric identification techniques relying on image processing. Images are two-dimensional, requiring sophisticated and computationally intensive algorithms, the analysis of which is often complicated by random orientation and variable scaling. Voice recognition is an example of biometric identification amenable to time series analysis, an inherently simpler one-dimensional process.

The simplest biometric identifiers can be expressed as a single parameter, such as height or weight. Single parameter identifiers have been the only quantitative means of identification throughout most of history. The price of simplicity is the loss of specificity, and in the case of weight, the lack of constancy over time. Nevertheless, single-parameter biometrics remain effective identifying factors, as is obvious from their continued use.

Identity tracking/confirmation is the process of following the whereabouts of a known subject moving unpredictably among similar individuals, perhaps with deceptive intent. Tracking/confirmation is somewhat simpler than identification, because it merely requires distinguishing the subject from all others rather than distinguishing every individual from every other, and because continuous rather than episodic data are available. Biometric identity tracking/confirmation is the continuous verification that a body-mounted sensor has remained on the subject, and has not been surreptitiously transferred to an impostor. For the purposes of this application, the term "biometric identification" should be broadly construed to encompass both biometric identification in its narrower sense, as described above, and identity tracking/confirmation.

SUMMARY OF THE INVENTION

This invention provides a portable testing unit for biometric identity confirmation for use with an external security station. The portable testing unit includes a housing with an orifice to receive a breath sample from the test subject, a spirometric sensor, and a pulse sensor adjacent to the orifice. A processor analyzes spirometric data from the spirometric sensor and simultaneous pulse wave data from the pulse sensor during the breath sample, together with stored subject characterization data for a known subject to confirm whether the identity of the test subject matches the known subject. A communications link enables the processor to communicate to the external station whether the identity of the test subject matches the known subject. For example, this can be used to control access to a secure facility or computer, authenticate the identity of a party in a financial transaction, or confirm the identity of the subject of an alcohol monitoring test.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which.

DETAILED DESCRIPTION OF THE INVENTION

Figure 1:
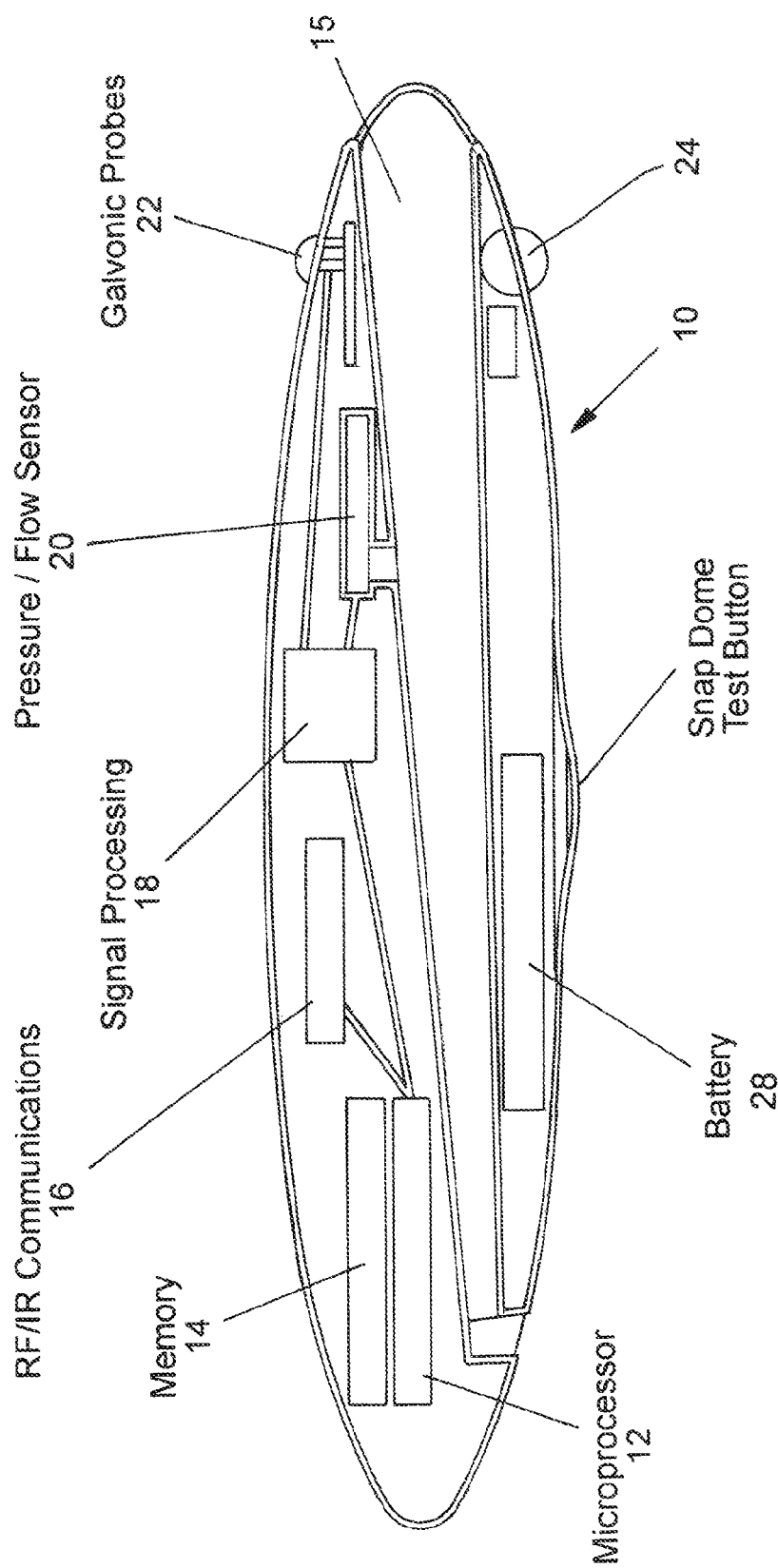
FIG. 1 is a simplified cross-sectional view of the portable testing unit 10.
Figure 2:
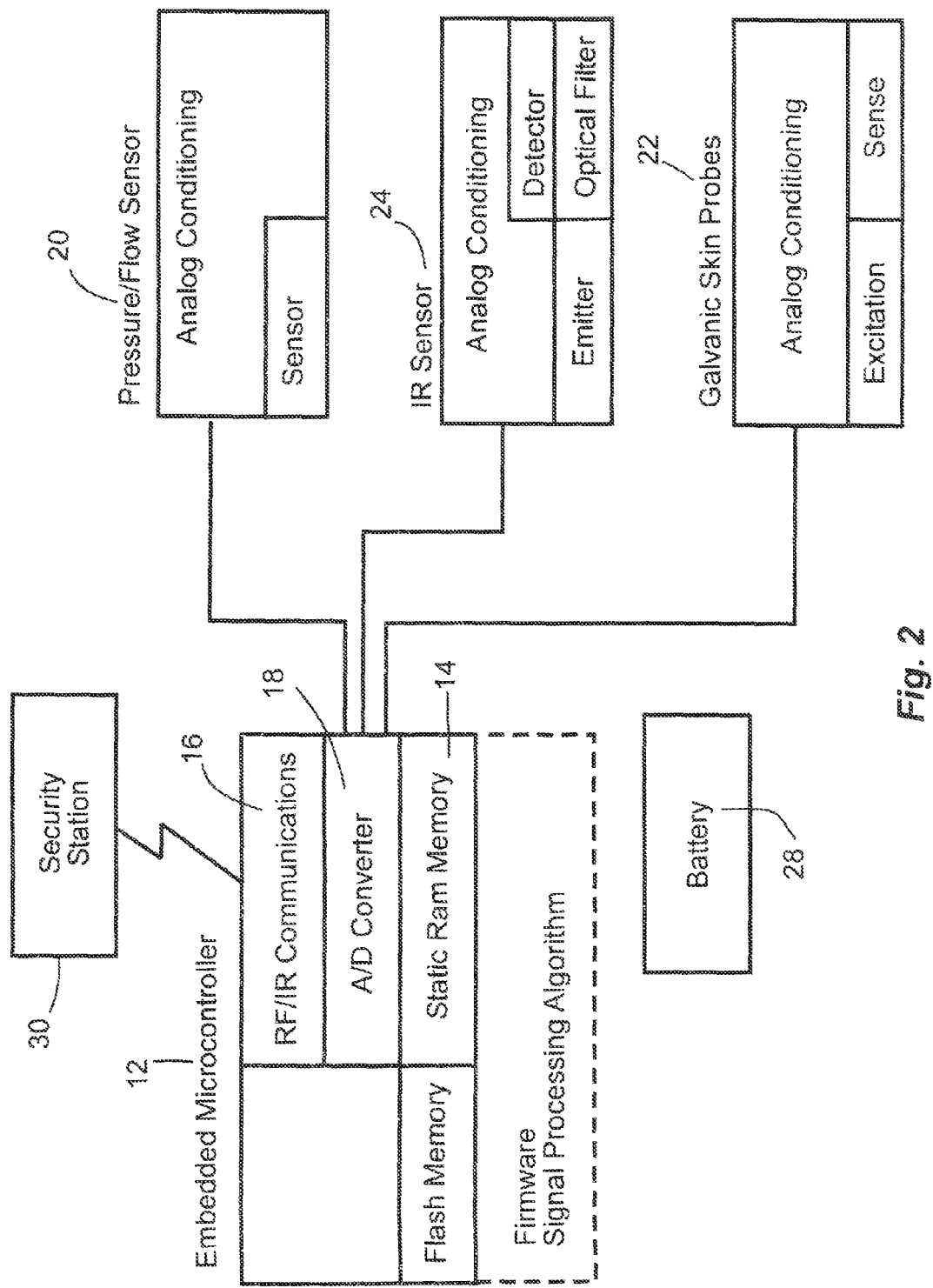
FIG. 2 is a system block diagram of the portable testing unit 10.

Turning to FIG. 1, a simplified cross-sectional view is illustrated showing one possible embodiment of the present invention. FIG. 2 is a corresponding system block diagram of the portable testing unit 10. This portable testing unit 10 is designed to confirm an individual's identity through the simultaneous measurement of their exhaled breath characteristics and their pulse waveform characteristics. When paired via a communications link to an external security station 30, the portable testing unit 10 can be employed to provide secure access of any type including facilities, cars, electronic devices and secure financial transactions.

Figure 3:
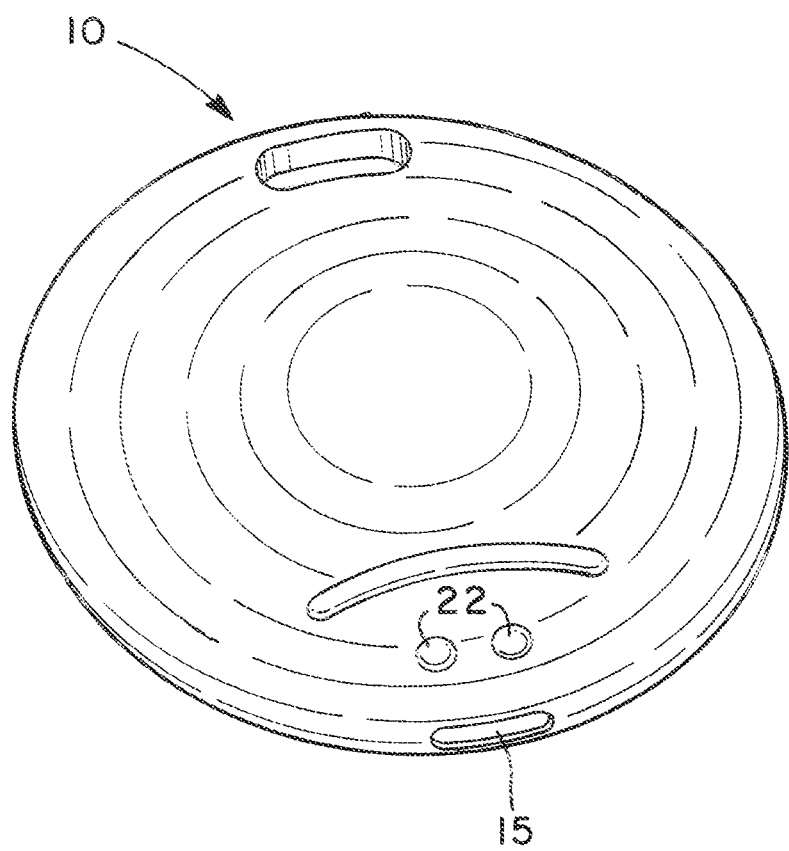
FIG. 3 is a top perspective view of the portable testing unit 10.

FIG. 3 is a top perspective view of an embodiment of the portable testing unit 10 with a disc-shaped housing having a diameter of about 1.75 inch. Returning to FIGS. 1 and 2, the testing unit 10 contains a pressure/flow transducer 20 within an orifice 15 extending through the testing unit 10 for generating spirometric data during breath samples provided by the subject. A pulse sensor 24 is located adjacent to the orifice 15 to generate pulse waveform data simultaneous with the spirometric data during each test. Preferably, the pulse sensor 24 has a 910 nm IR emitter and detector with two ball lenses. In this embodiment, the infrared emitter transmits infrared light through a ball lens that protrudes slightly into the lip of the test subject. The infrared detector receives and measures infrared light traveling from the infrared emitter through a portion of the lip to a second ball lens protruding slightly into the lip. These ball lenses are adjacent to the orifice 15, and are at a predetermined distance from one another. Alternatively, a piezoelectric sensor (e.g., a piezoelectric film) could be used as the pulse sensor 24. Two galvanic probes 22 ensure that subject's lips remain in contact with the orifice 15 throughout the breath sample.

As illustrated in FIG. 2, the test unit 10 also includes a microprocessor 12 with on-board memory 14, and an analog-to-digital converter 18 as an interface between the sensors 20, 24 and the processor 12. An R/F transceiver 16 enables the testing unit 10 to communicate with an external security station 30. Finally, the testing unit 10 includes a snap dome switch 26 to initiate a test, and a battery 28 to power the remaining components.

The testing unit 10 is initially assigned by a supervising party to an individual wishing to access secure areas/systems/ devices that the testing unit 10 is paired with. At this time the individual will be required to complete an enrollment process under supervision of the assigning party. During the enrollment process, the subject is required to provide a number of breath samples that enable the processor 12 to generate subject characterization data derived from the spirometric data and pulse wave data to identify the known subject. This subject characterization data is stored in the memory 14 for later use. In the subsequent operational mode, the testing unit 10 is used to confirm the person's identity through analysis of spirometric data and pulse wave data from subsequent breath samples.

In the preferred embodiment of the present invention, the testing unit 10 simultaneously performs breath print spirometry and lip pulse photoplethysmography. The Applicants' previous U.S. patent application Ser. No. 13/169,603, entitled "Breath Alcohol Sampling System With Spirometric Client Identity Confirmation," filed on Jun. 27, 2011, and U.S. Provisional Patent Application Ser. No. 61/589,084, entitled "System For Biometric Identity Confirmation," filed on Jan. 20, 2012, (which are hereby incorporated by reference) describe a number of techniques for breath print spirometry for client identity confirmation during breath alcohol microsampling that can also be employed in the present invention. In the preferred embodiment of the present invention, the spirometry sensor 20 uses a pressure-sensitive diaphragm to infer the exhaled volumetric airflow rate, which can be characterized by the duration of exhalation (T), the force vital capacity (V), and the normalized shape of the flow versus time curve (S). However, it should understood that other types of spirometric sensors could be substituted, and that other spirometric data could be used for subject characterization.

Providing repeatable spirometric data requires the subject to exert labial pressure on the mouthpiece or orifice 15 of the testing unit 10 to ensure a good seal. This affords the opportunity to perform simultaneous lip pulse photoplethysmography of the pulse wave using, for example, an infrared light-emitting diode (IR LED) and detector built into the housing of the testing unit 10 adjacent to the orifice 15 and in contact with subject's lip. The Applicants' previous U.S. patent application Ser. No. 13/079,219, entitled "Biometric Identification System Using Pulse Waveform," filed on Apr. 4, 2011, (which is hereby incorporated by reference) describes a number of approaches to using the pulse waveform for subject identity confirmation, which can also be readily adopted in the present invention. Subject pulse waveform characteristics such as rate, excursion and shape can be measured before, during and just after exhalation. Several aspects of the pulse waveform and its interaction with the spirometric data may be exploited, such as: (1) The baseline pulse waveform itself, before exhalation; (2) The degree of exsanguination of the labial tissue as pressure is applied to achieve a seal prior to exhalation; (3) The possible acceleration and lessening excursion of the pulse as exhalation proceed; or (4) The return to normal sanguinity, rate, and excursion after exhalation has ended. The resulting combination of involuntary autonomic and physiological characteristics, subconscious idiosyncrasies and deliberate practices are believed to be quite specific to the subject, thereby providing a powerful identity authentication technique.

The following is a description of the operational mode of the present invention. When an individual wishes to access a secure system/device/area, the subject simply presses the test button 26 and places the inlet orifice 15 to their mouth with their upper lip on the galvanic probes 22 and lower lip on the IR ball lens of the pulse sensor 24. The subject then exhales completely into the device. Simultaneously, the IR emitter of the pulse sensor 24 transmits light at a wavelength of about 910 nm into the person's lower lip through a ball lens protruding slightly into the lip of the test subject. The IR detector or photodiode of the pulse sensor 24 measures infrared light that has traveled through the lip from the IR emitter and entered a second ball lens protruding slightly into the test subject's lip at a distance from the first ball lens. Simultaneously, the breath sample travels through the inlet orifice 15 to a flow restriction in the exit port generating a positive pressure monitored by the spirometric sensor 20. The galvanic probes 22 act as a switch to initiate the IR data acquisition and as a safety device to shut off the IR emitter and fail the test in the event a person's lip is removed during the testing period. During this period, the testing unit 10 simultaneously measures exhaled breath with the spirometric sensor 20 and pulse characteristics with the pulse sensor 24. This data is sent from the spirometric transducer 20 and pulse sensor 24 to the ND converter 18 and is stored in memory 14 for subsequent processing by the microprocessor 12. These data are compared with the original subject characterization data from the enrollment period to confirm the subject's identity. In the event the identity is not confirmed, an encrypted lockout code is transmitted along with the testing unit's unique identifier code. In the event the individual's identity is confirmed the testing unit 10 transmits a unique encrypted identifier and an enable code to the security station 30 for a predetermined time frame. Access devices that have been paired with this unique testing unit 10 will provide or deny access based on the identity confirmation test results.

The present invention provides a number of key advantages over the prior art. First, once a testing unit 10 is assigned to and enrolled by an individual, only that individual's identity can be confirmed by the testing. In the event the testing unit 10 is lost, it is useless to anyone that may find it. This is certainly not the case with a traditional office key, car key, house key, RFID key, swipe access card or credit/debit card.

Second, due to the testing unit's ability to complete an identity confirmation test in advance of entering the facility and transmit an enable access code for a period of time, it can dramatically reduce waiting time for employees entering secure facilities, in contrast to conventional facial recognition, retina, fingerprint and voice identification methods as well as retail credit/debit card transactions. This new level of credit/debit card security is believed to have the potential to save billions of dollars annually in credit card fraud.

The same testing unit 10 may be assigned to more than one individual such as a number of members of a family. In this instance each individual would be enrolled on the testing unit 10 and would subsequently confirm the identity of each individual and record the person accessing the facility or device at that time.

Finally, the present invention may be programmed to provide different time periods of access for different levels of required security. For example, the testing unit 10 could be programmed to provide a fifteen-minute enable period for a home security system, five minutes to enable a car start, one minute for a secure office, six hours for a low level computer, and 500 milliseconds for a debit/credit/ATM card or financial transaction. It is anticipated that this device could be used by any type of secure facility, business, residence, automobile, mechanical or electronic device, debit/credit/ATM card terminal providing a convenient and enhanced level of access/transaction security.

The above disclosure sets forth a number of embodiments of the present invention described in detail with respect to the accompanying drawings. Those skilled in this art will appreciate that various changes, modifications, other structural arrangements, and other embodiments could be practiced under the teachings of the present invention without departing from the scope of this invention as set forth in the following claims.

We claim:

1. An apparatus for biometric confirmation of the identity of a test subject having a pulse and a respiratory cycle, said apparatus comprising:
   a housing with an orifice for receiving a breath sample from a test subject;
   a spirometric sensor generating spirometric data from the breath sample;
   a pulse sensor adjacent to the orifice and in contact with the test subject during the breath sample, said pulse sensor simultaneously generating pulse wave data for the test subject during the breath sample and having:
   (a) an infrared emitter adjacent to the orifice transmitting infrared light into the lip of the test subject; and
   (b) an infrared detector adjacent to the orifice receiving and measuring the infrared light traveling through the lip of the test subject from the infrared emitter; and
   (c) a ball lens protruding into the lip of the test subject adjacent to the orifice for receiving infrared light traveling from the infrared emitter through the lip of the test subject for the infrared detector;
   stored subject characterization data based on spirometric data and pulse wave data for a known subject; and
   a processor analyzing the spirometric data from the spirometric sensor, the pulse wave data from the pulse sensor, and the subject characterization data for the known subject to confirm whether the identity of the test subject matches the known subject.

2. The apparatus of claim 1 further comprising a ball lens protruding into the lip of the test subject adjacent to the orifice for transmitting infrared light from the infrared emitter into the lip of the test subject.

3. The apparatus of claim 1 further comprising galvanic probes adjacent to the orifice and in communication with processor to ensure that the lips of the test subject remain in contact with the orifice throughout the breath sample.

4. The apparatus of claim 1 further comprising a transceiver controlled by the processor communicating to the external station whether the identity of the test subject matches the known subject.

5. The apparatus of claim 1 wherein the processor includes an initial enrollment mode in which spirometric data and pulse wave data for a known subject are analyzed to generate the subject characterization data.

6. A portable testing unit for biometric identity confirmation of a test subject having a pulse and a respiratory cycle for use with an external station having a communications link with the testing unit, said portable testing unit comprising:
   a housing with an orifice receiving a breath sample from a test subject;
   a spirometric sensor generating spirometric data from the breath sample;
   a pulse sensor adjacent to the orifice and in contact with the test subject during the breath sample, said pulse sensor simultaneously generating pulse wave data for the test subject during the breath sample and having:
   (a) an infrared emitter adjacent to the orifice transmitting infrared light into the lip of the test subject; and
   (b) an infrared detector adjacent to the orifice receiving and measuring the infrared light traveling through the lip of the test subject from the infrared emitter; and
   (c) a ball lens protruding into the lip of the test subject adjacent to the orifice for receiving infrared light traveling from the infrared emitter through the lip of the test subject for the infrared detector;
   stored subject characterization data based on spirometric data and pulse wave data for a known subject;
   a processor analyzing the spirometric data from the spirometric sensor, the pulse wave data from the pulse sensor, and the subject characterization data for the known subject to confirm whether the identity of the test subject matches the known subject; and
   a transceiver controlled by the processor communicating to the external station whether the identity of the test subject matches the known subject.

7. The apparatus of claim 6 further comprising a ball lens protruding into the lip of the test subject adjacent to the orifice for transmitting infrared light from the infrared emitter into the lip of the test subject.

8. The apparatus of claim 6 further comprising galvanic probes adjacent to the orifice and in communication with processor to ensure that the lips of the test subject remain in contact with the orifice throughout the breath sample.

9. The apparatus of claim 6 wherein the processor includes an initial enrollment mode in which spirometric data and pulse wave data for a known subject are analyzed to generate the subject characterization data.

* * * * *